United States Patent [19]

Bellinger et al.

[11] 4,203,741
[45] May 20, 1980

[54] SEPARATE FEED ENTRY TO SEPARATOR-CONTACTOR IN GAS SEPARATION

[75] Inventors: Robert M. Bellinger; Michael L. Gray, both of Bartlesville, Okla.

[73] Assignee: Phillips Petroleum Company, Bartlesville, Okla.

[21] Appl. No.: 915,687

[22] Filed: Jun. 14, 1978

[51] Int. Cl.² ............................................. F25J 3/02
[52] U.S. Cl. ........................................ 62/24; 62/23; 62/38; 62/26
[58] Field of Search ............... 62/23, 27, 28, 38, 124, 62/26

[56] References Cited

U.S. PATENT DOCUMENTS

| | | | |
|---|---|---|---|
| 2,265,558 | 12/1941 | Ward et al. | 62/23 |
| 3,292,381 | 12/1966 | Bludworth | 62/27 |
| 4,061,481 | 12/1977 | Campbell et al. | 62/38 |

OTHER PUBLICATIONS

Evolution in Design, R. L. McKee, Gas Processors Association, pp. 123–125, Mar. 21–23, 1977.

*Primary Examiner*—Norman Yudkoff

[57] ABSTRACT

In the separation of low boiling gases such as ethane or propane and heavier from a gas stream such as natural gas, a first portion of the feed is heat exchanged with an overhead from a downstream stripper column, such as a demethanizer, a second portion is heat exchanged with a stream from a lower portion of said stripper column, and these two portions passed as separate streams to a separator-contactor. The first stream is added at a point above the second. This results in an increase in the recovery of liquid products.

13 Claims, 1 Drawing Figure

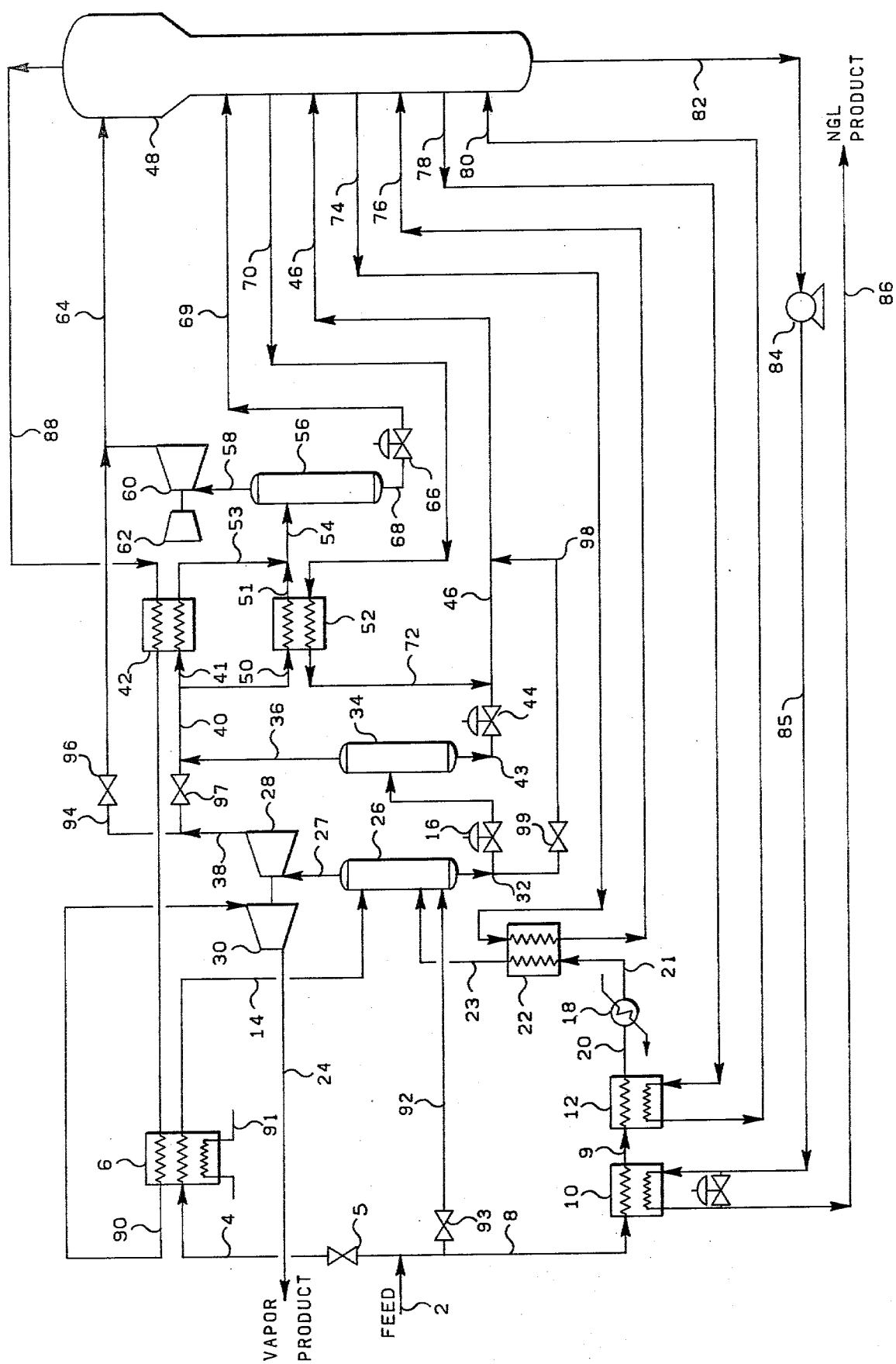

SEPARATE FEED ENTRY TO SEPARATOR-CONTACTOR IN GAS SEPARATION

BACKGROUND OF THE INVENTION

This invention relates to the separation of higher molecular weight components from lower molecular weight components in a fluid stream. In a specific embodiment, it relates to the separation of the ethane or propane and higher molecular weight components from a natural gas stream containing methane.

Natural gas as it comes from the ground generally is not suitable for use directly without some processing. The basic processing operations carried out in a natural gas plant are to first remove acid gases such as $CO_2$ and $H_2S$ and then to pass the gas through a dehydration means to remove water. The resulting product can then be used as a fuel. However, such streams generally contain a substantial amount of higher molecular weight components such as ethane, propane and, to a lesser extent, butanes, and higher components. The heavier components are of greater value as chemical feedstocks than they are as a fuel. Consequently, it is desirable to separate either all of the heavier components from the methane or else separate propane and heavier from the methane and ethane.

It has long been known to separate ethane and higher components from methane by the use of an expander wherein a natural gas feed stream is passed to a high pressure separator and the vapor taken off and passed to an expander with the resulting vapor going to the upper portion of a stripper such as a demethanizer and the liquid from the separator going to the lower portion of the stripper. Such a system is not as efficient as would be desired, however.

SUMMARY OF THE INVENTION

It is an object of this invention to increase the efficiency of the removal of heavier components from a gas stream;

It is a further object of this invention to increase the volume of gas to an expander;

It is a still further object of this invention to put less heat into the side reboiler of the stripper column; and It is still yet a further object of this invention to provide improved separation of propane and heavier components from methane in a natural gas processing plant.

In accordance with this invention, a first portion of a gas feed is heat exchanged with an overhead from a downstream stripper column, a second portion is heat exchanged with a stream from a lower portion of said stripper column and the two streams added separately to a separator-contactor, the first being introduced at a point above the second.

BRIEF DESCRIPTION OF THE DRAWING

In the drawing, forming a part hereof, there is shown in schematic form a portion of a natural gas plant, downstream from a dehydrator, employing the invention.

DESCRIPTION OF THE PREFERRED EMBODIMENTS

The principle of this invention wherein the feed is separated, heat exchanged as separate streams with the overhead and bottoms respectively, of a downstream stripper column and then introduced as separate streams to a separator-contactor is broadly applicable to any separation of higher and lower molecular weight gaseous components (for instance, separating propane and higher from ethane or ethane and higher from methane. However, it will be described hereinafter in terms of the preferred embodiment wherein propane and higher components are separated from the methane and ethane in a dehydrated natural gas stream.

Referring now to the Figure, line 2 carries feed which is a natural gas stream which has been subjected to conventional processes to remove acid gases such as $CO_2$ and $H_2S$ and which has been subjected to conventional dehydration processes to remove water. This natural gas vapor feed line stream is then divided and the first portion passes via gas line 4 to gas-gas residue exchanger 6 for the purpose of recovering refrigeration from the residual gas which is primarily methane and ethane. The proportion of the feed passing via line 4 is adjusted by means of a valve 5 so as to efficiently utilize the refrigeration available in the residual gas contained in line 90. Additional refrigeration can be supplied by refrigeration means 91, if desired. This can be, for instance, a propane refrigeration cycle. The thus cooled first feed portion then passes to an upper portion of separation and contacting zone 26. The second portion of the feed passes via gas line 8 to product heat exchanger 10 and thence via line 9 to stripper column bottom reboiler 12 and thence via line 20 to chiller (optional) 18, and thence via line 21 through second side reboiler 22 (the first side reboiler will be described hereinbelow). The thus cooled feed in line 23 is then passed to a lower or intermediate portion of said separator-contactor 26 below the entry of said first portion. Generally, the introduction point for line 23 is below that of line 14, a distance of at least 20 percent of the height of separator-contactor 26. Separator-contactor 26 contains conventional packing or trays. Liquid which is warmer than it would have been if the feed had been introduced at a common point is drawn off the bottom of separator-contactor 26 via liquid line 32, and the vapor which is cooler than it would have been if the feed had been introduced to the separator-contactor at a common point is drawn off the top via vapor line 27 and passed to the first expander (expansion zone) 28. A portion of the feed can be passed directly to separator-contactor 26 via line 92 by opening valve 93, if desired. Expander 28 drives compressor 30 to compress the vapor product, for instance. Of course, expander 28 can drive any mechanical means such as a generator, and the like, if desired. Also, expander 28 and the subsequent expanders, if any, can be connected by a common shaft to a single compressor or generator means, if desired, or to separate means as shown herein. The thus cooled expanded fluid stream from first expander 28 is drawn off via line 38. This can be fed directly to the top of column 48 by eliminating the second expander 60 and connecting line 38 directly to line 64 via line 94 by opening valve 96 and closing valve 97; in this case the bottoms from separator-expander 26 are fed directly to column 48 by connecting line 32 with line 46 by means of line 98 by opening valve 99 and closing valves 16, 44 and 66.

If two expanders are used in series as is shown in the drawing, liquid drawn off from separator-contactor 26 via line 32 passes through first expansion valve 16 (valve 99 being closed) and thence to a flash separation zone 34 operating preferably at essentially the discharge pressure of expander 28, or it can go directly to column 48 via line 46 thus eliminating separation zone 34. The liquid from feed separator 34 passes via line 43 through second expansion valve 44 and thence via line 46 to stripper column 48. The combined flashed vapor and expansion vapor stream 40 which may contain some liquid can be split and the first portion passed via cold exchange gas line 41 to cold gas exchanger 42, which serves to both recover refrigeration from the very cold gas from the top of the stripper and to cool stream 41. The second portion of stream 40 can be passed via line 50 to first side reboiler 52. The fluids from exchanger 42 and reboiler 52 are withdrawn by lines 53 and 51, respectively, and can be passed via combined stream line 54 to low pressure separator (second expander inlet separation zone) 56. Alternatively, streams 53 and 51 can be added separately at upper and lower portions of column 56 (in which case it would contain packing or trays) instead of, or in addition to, the addition of feed from lines 14 and 23 separately to separator-contactor 26. Low pressure separator 56 operates as an expander inlet separator for the second expander in the same manner that high separator-contactor 26 operates as the expander inlet separator for the first expander 28. The vapor from separator 56 passes via vapor line 58 to second expander 60 which drives compressor 62. The vapor (which may contain some liquid) from expander 60 is withdrawn via line 64 and passed to a stripping zone 48. The liquid is withdrawn from separator 56 via line 68, passed through third expansion valve 66, and thence to column 48 via line 69. Generally, this entry point is below the entry of line 64 although lines 64 and 69 can be combined. In the embodiment where two expanders are used, a major portion of the liquid withdrawn from separator-contactor 26 is passed to stripper 48 at a point below the point of entry of line 64, a small amount being combined with the vapor stream line 40 and ultimately being introduced into stripper 48 via line 64. With only one expander, all of the liquid is passed directly to stripper 48.

Liquid is withdrawn from column 48 via line 70 and passed to first side reboiler 52 where it picks up sufficient heat to heat this portion of column 48 on being returned thereto via lines 72 and 46. Stripper column 48 like separator-contactor 26 contains conventional packing or trays but is like the lower part of a distillation column by virtue of having provision for reboiling as shown whereas separator-contactor 26 does not except in the alternative embodiment where uncooled feed is added to the bottom thereof. If everything heavier than methane is being separated from the feed, then column 48 is simply a conventional demethanizer. A second liquid stream is withdrawn from column 48 via line 74 and passed to second side reboiler 22 where it picks up sufficient heat to heat the lower intermediate portion of column 48 on being passed back thereto via line 76. A third liquid stream is withdrawn from column 48 via line 78 and passed to bottom reboiler 12 where it picks up sufficient heat to heat the bottom of column 48 on being returned thereto via line 80.

Finally, the bottom product from column 48 which is predominantly propane is withdrawn via line 82 and passed by pump 84 and line 85 to product heat exchanger 10 where it is heated to essentially ambient temperature and discharged via line 86 as the NGL product of the process. Alternatively, line 82 can bypass exchanger 10 and the product NGL taken off without being heat exchanged with the feed. In any event, a liquid stream (78 and/or 82) from a lower portion of column 48 is heat exchanged with feed in line 8.

The residue gas from the top of the demethanizer 48 is withdrawn via line 88. This residue gas is primarily ethane, methane and nitrogen and is passed through cold gas exchanger 42 (if two expanders are used) and gas-gas residue exchanger 6 where it is heated to the desired temperature for discharge. Residue stream 90 generally is compressed by means of compressor 30 and/or 62 and discharged via line 24 for use in this form as a fuel source, i.e., natural gas for firing furnaces, and the like.

The chiller 18, if used, is cooled generally by some external source, such as propane refrigerant. Except for chiller 18, refrigerant 91 and pump 84, which may be powered by a relatively small electric motor, most of the energy for this operation comes from the potential energy stored in the feed gas as a result of it being under compression.

The initial pressures for feed line 2 are generally in the neighborhood of 500 to 750 psia (3.45 to 5.17 MPa). If only a single expander is used, the pressure is generally reduced to 120 psia (0.83 MPa) to 200 psia (1.38 MPa). The invention is applicable to systems, however, having initial pressure in the range of 400 to 1,000 psia (2.76 to 6.89 MPa), preferably 500 to 875 psia (3.45 to 6.03 MPa). The downstream stripping zone, i.e., demethanizer, pressures can vary from 50 to 450 psia (0.34 to 3.1 MPa), preferably from 100 to 350 psia (0.689 to 2.4 MPa).

The following calculated illustrative embodiment is based on calculations which have been found to agree closely with typical operating conditions in actual operation.

CALCULATED ILLUSTRATIVE EMBODIMENT

A natural gas stream is passed through a conventional process for removing acid gases and, thence, through a conventional process for dehydration and then to a plant as shown in the drawing using the option of only one expander, i.e., with valves 97 and 16 closed and valves 96 and 99 open. The calculated pressures, temperatures and flow rates of the various streams are shown in Table I. Table II shows the calculated advantage for the invention as compared with a control run using gallons/day as the units.

Table I

| Stream No. | 2 | (%) | 4 | 8 | 14 | 20 | 23 | 27 | 32 | 64 | 88 | 86 | 24 |
|---|---|---|---|---|---|---|---|---|---|---|---|---|---|
| | | | | | MATERIAL BALANCE LB MOLS/HR | | | | | | | | |
| Nitrogen | 129.8 | (4.7) | 64.1 | 65.7 | | | | 128.5 | 1.3 | | 129.8 | — | |
| Carbon Dioxide | 4.7 | (0.2) | 2.3 | 2.4 | | | | 4.3 | 0.4 | | 4.7 | — | |
| Methane | 2,228.3 | (81.2) | 1,100.8 | 1,127.5 | | | | 2,165.2 | 63.1 | | 2,228.3 | — | |
| Ethane | 220.4 | (8) | 108.9 | 111.5 | | | | 175.8 | 44.6 | | 192.6 | 27.8 | |
| Propane | 100.7 | (3.7) | 49.8 | 50.9 | | | | 37.1 | 63.6 | | 6.2 | 94.5 | |
| i-Butane | 12.6 | (0.5) | 6.2 | 6.4 | | | | 1.6 | 11.0 | | — | 12.6 | |
| n-Butane | 26.9 | (1) | 13.3 | 13.6 | | | | 2.1 | 24.8 | | — | 26.9 | |
| i-Pentane | 6.3 | | 3.1 | 3.2 | | | | 0.2 | 6.1 | | | 6.3 | |
| n-Pentane | 6.6 | (0.8) | 3.3 | 3.3 | | | | 0.1 | 6.5 | | | 6.6 | |
| Hexanes | 4.1 | | 2.0 | 2.1 | | | | — | 4.1 | | | 4.1 | |

Table I-continued

| Stream No. | 2 | (%) | MATERIAL BALANCE LB MOLS/HR | | | | | | | | | |
| --- | --- | --- | --- | --- | --- | --- | --- | --- | --- | --- | --- | --- |
| | | | 4 | 8 | 14 | 20 | 23 | 27 | 32 | 64 | 88 | 86 | 24 |
| Heptanes+ | 4.4 | | 2.2 | 2.2 | | | | | 4.4 | | | 4.4 | |
| Total | 2,744.8 | | 1,356.0 | 1,388.8 | | | | 2,514.9 | 229.9 | | 2,561.6 | 183.2 | |
| Temp., °F. | 84 | | 84 | 84 | −94 | 45 | 20 | −55 | −6 | −141 | −126 | 70 | 144 |
| Temp., °C. | 29 | | 29 | 29 | −70 | 7 | −7 | −48 | −21 | −96 | −88 | 21 | 62 |
| Pressure, Psia | 600 | | 600 | 600 | 590 | 595 | 590 | 590 | 590 | 140 | 140 | 140 | 173 |

Table II

MATERIAL BALANCE, GAL. PER DAY

| Stream No. | 86 | |
| --- | --- | --- |
| | NGL Product | |
| | Control | Invention |
| Carbon Dioxide | 0.025 | 0.020 |
| Methane | 0.001 | 0.001 |
| Ethane | 7660.164 | 7699.340 |
| Propane | 22476.977 | 22933.230 |
| Isobutane | 3688.575 | 3696.605 |
| n-Butane | 7627.766 | 7634.305 |
| Isopentane | 2117.427 | 2117.560 |
| n-Pentane | 2211.845 | 2211.927 |
| Hexanes | 1584.339 | 1584.338 |
| Heptanes | 1865.218 | 1865.217 |
| Total | 49232.324 | 49742.535 |

As can be seen, the use of the invention is calculated to give a 510 gal. per day increase in NGL recovery.

While this invention has been described in detail for the purpose of illustration, it is not to be construed as limited thereby but it is intended to cover all changes and modifications within the spirit and scope thereof.

I claim:

1. A process comprising:
   (a) dividing a fluid feed stream having higher and lower molecular weight hydrocarbons into at least first and second portions;
   (b) passing said first portion of said feed stream into heat exchange relationship with overhead from a downstream stripping zone to cool said first portion of said feed stream;
   (c) passing said second portion of said feed stream into heat exchange relationship with a stream from a lower portion of said downstream stripping zone to cool said second portion of said feed stream, said first portion of said feed stream being cooled to a lower temperature than said second portion of said feed stream;
   (d) passing said thus cooled first portion of said feed stream to an upper portion of a separation and contacting zone;
   (e) passing said thus cooled second portion of said feed stream to said separation and contacting zone at a point at least 20 percent of the height of said separation and contacting zone below the point of said cooled first portion of said feed stream;
   (f) withdrawing a vapor stream from an upper portion of said separation and contacting zone and passing said vapor stream to an expansion zone where said vapor stream is expanded to cool said vapor stream and produce external work;
   (g) withdrawing a cooled expanded fluid stream from said expansion zone and passing said thus cooled fluid stream to an upper portion of said stripping zone;
   (h) withdrawing liquid from a lower portion of said separation and contacting zone;
   (i) passing at least a major portion of the thus withdrawn liquid of (h) to said stripping zone at a point below the introduction of said cooled fluid stream of (g) and above the point said stream of (c) is withdrawn;
   (j) withdrawing said overhead from said heat exchange with said first portion of said feed as a vapor product of the process; and
   (k) withdrawing bottom product from said stripping zone as a liquid product of said process.

2. A process according to claim 1 wherein said feed is natural gas.

3. A method according to claim 2 wherein said natural gas has been treated to remove acid gases and water.

4. A method according to claim 3 wherein said natural gas comprises methane, ethane, propane and smaller amounts of higher molecular weight hydrocarbons.

5. A method according to claim 4 wherein said natural gas comprises predominantly methane with smaller amounts of ethane, propane, butanes, and nitrogen.

6. A method according to claim 1 wherein said vaporous product of said process is predominantly ethane, methane and nitrogen and said liquid product recovered from the bottom portion of said fractionation zone comprises propane and higher molecular weight hydrocarbons with only a minor amount of methane present.

7. A method according to claim 6 wherein said fluid feed stream of (a) is at a pressure within the range of 500 to 750 psia and said stripping zone is operated at a pressure within the range of 50 to 450 psia.

8. A method according to claim 1 wherein said feed comprises about 4.7 percent nitrogen, 0.2 percent carbon dioxide, 81.2 percent methane, 8 percent ethane, 3.7 percent propane, 0.5 percent isobutane, 1 percent n-butane, and 0.8 percent $C_5+$ hydrocarbons, said feed is at a pressure of about 600 psia and said stripper is operated at a pressure of about 140 psia.

9. A method comprising:
   (a) dividing a fluid feed stream into three portions;
   (b) passing a first portion of said feed stream into heat exchange relationship with overhead from a downstream stripping zone to cool said first portion of said feed stream;
   (c) passing a second portion of said feed stream into heat exchange relationship with a stream from a lower portion of said downstream stripping zone to cool said second portion of said feed stream;
   (d) passing said thus cooled first portion of said feed stream to an upper portion of a separation and contacting zone;
   (e) passing said thus cooled second portion of said feed stream to said separation and contacting zone at a point below the point of said cooled first portion of said feed stream;
   (f) passing a third portion of said feed stream to said separation and contacting zone, said third portion being introduced into said separation and contacting zone without cooling at a point below the points of introduction of the first and second portions;

(g) withdrawing a vapor stream from an upper portion of said separation and contacting zone and passing said vapor stream to an expansion zone where said vapor stream is expanded to cool said vapor stream and produce external work;

(h) withdrawing a cooled expanded fluid stream from said expansion zone and passing said thus cooled fluid stream to an upper portion of said stripping zone;

(i) withdrawing liquid from a lower portion of said separation and contacting zone;

(j) passing at least a major portion of the thus withdrawn liquid of (i) to said stripping zone at a point below the introduction of said cooled fluid stream of (h) and above the point said stream of (c) is withdrawn;

(k) withdrawing said overhead from said heat exchange with said first portion of said feed as a vapor product of the process; and (l) withdrawing bottom product from said stripping zone as a liquid product of said process.

10. A process according to claim 1 wherein said expanded fluid of (g) is passed through a second expansion zone before being introduced into said stripping zone.

11. A method according to claim 1 wherein said first portion of said feed stream is subjected to additional refrigeration before being passed to said separation and contacting zone.

12. A method according to claim 1 wherein said stream from a lower portion of said stripping zone is said bottom product of (k).

13. A method according to claim 1 wherein said stream from a lower portion of said stripping zone is taken off just above the bottom of said stripping zone.

* * * * *